(12) United States Patent
Tashiro et al.

(10) Patent No.: US 7,642,094 B2
(45) Date of Patent: Jan. 5, 2010

(54) METHOD OF MEASURING BIODEGRADATION RATE OF UNNATURAL ORGANIC COMPOUND

(75) Inventors: Hironori Tashiro, Chiba (JP); Shinji Ito, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 610 days.

(21) Appl. No.: 10/539,805

(22) PCT Filed: Dec. 12, 2003

(86) PCT No.: PCT/JP03/15992

§ 371 (c)(1),
(2), (4) Date: Feb. 7, 2006

(87) PCT Pub. No.: WO2004/055511

PCT Pub. Date: Jul. 1, 2004

(65) Prior Publication Data

US 2006/0160228 A1    Jul. 20, 2006

(30) Foreign Application Priority Data

Dec. 18, 2002    (JP) .............................. 2002-366721

(51) Int. Cl.
*G01N 23/00* (2006.01)
*G01N 31/00* (2006.01)
*G01N 33/24* (2006.01)

(52) U.S. Cl. ............................. 436/57; 436/19; 436/25; 436/27

(58) Field of Classification Search .................. 436/19, 436/57, 25, 27
See application file for complete search history.

(56) References Cited

U.S. PATENT DOCUMENTS 5,284,995 A * 2/1994 Melvin ....................... 588/313
6,287,847 B1 * 9/2001 Knowles et al. ........... 435/262.5

FOREIGN PATENT DOCUMENTS

JP    05-180830    7/1993

OTHER PUBLICATIONS

Robert J. Larson: "Comparison of biodegradation rates in laboratory screening studies with rates in natural waters", Residue Reviews, vol. 85, pp. 159-171.1983.
Currie, L. (2004), "The Remarkable Metrological History of Radiocarbon Dating II", J. Res. Natl. Inst. Stand. Technol. 109: 185-217.

* cited by examiner

*Primary Examiner*—Vickie Kim
*Assistant Examiner*—Keri A Moss
(74) *Attorney, Agent, or Firm*—Oblon, Spivak, McClelland, Maier & Neustadt, L.L.P.

(57) ABSTRACT

Provided is a method of measuring a biodegradation rate of a non-natural organic compound in the presence of a biodegradation medium, characterized by including: measuring a concentration of a radioactive carbon isotope $^{14}C$ in a biodegradation medium; and measuring a biodegradation rate of a non-natural organic compound from a difference between the concentration of $^{14}C$ in the biodegradation medium and a concentration of $^{14}C$ in modern carbon. Further, a metal such as iron in the medium can be used as an internal standard. According to the method, a biodegradation rate of a non-natural organic compound can be measured safely, simply, rapidly, and accurately without providing any special measures against radiation.

14 Claims, 1 Drawing Sheet

METHOD OF MEASURING BIODEGRADATION RATE OF UNNATURAL ORGANIC COMPOUND

TECHNICAL FIELD

The present invention relates to a method of measuring a biodegradation rate of a non-natural organic compound. The present invention more specifically relates to a method of measuring a biodegradation rate of a non-natural organic compound safely, simply, rapidly, and accurately by utilizing change in a concentration of a radioactive carbon isotope $^{14}C$ from the modern carbon.

BACKGROUND ART

In order to measure directly a biodegradation rate of an organic compound, a radioactive carbon isotope $^{14}C$ must be organochemically enriched in a sample first. Next, the sample enriched with the radioactive carbon isotope $^{14}C$ is subjected to biodegradation, and a radiation dose of carbon dioxide generated in biodegradation is measured with a scintillation counter to determine an absolute amount of the radioactive carbon isotope $^{14}C$ in carbon dioxide generated in biodegradation of the organic compound. A ratio of the absolute amount of the radioactive carbon isotope $^{14}C$ in carbon dioxide to an absolute amount of the radioactive carbon isotope $^{14}C$ in the $^{14}C$-enriched sample used is calculated, to thereby determine the biodegradation rate of the organic compound.

However, in the measurement method, a series of measuring operations must be performed in a space provided with measures against radiation because radioactive $^{14}C$ is used. Thus, the measurement method has problems in that measurement of a radiation dose of carbon dioxide generated in biodegradation requires a long period of time, and that measurement errors are observed by disturbance of background radioactivity or the like in measurement of the radiation dose.

Therefore, development of a method of measuring a biodegradation rate of a non-natural organic compound rapidly and accurately without enriching a measurement sample with an expensive radioactive carbon isotope $^{14}C$ and without providing any special measures against radiation has been desired.

DISCLOSURE OF THE INVENTION

It is an object of the present invention to provide a method of measuring a biodegradation rate of a non-natural organic compound safely, simply, rapidly, and accurately with little measurement error without providing any special measures against radiation.

The inventors of the present invention have conducted intensive studies for attaining the above-described object, and have found that a biodegradation rate of a non-natural organic compound can be measured by utilizing a fact that a decaying radioactive carbon isotope $^{14}C$ decays completely in a non-natural organic compound and no $^{14}C$ remains therein, and by measuring a difference between a concentration of $^{14}C$ in carbon dioxide from a medium mixed with a measurement sample for biodegradation and a concentration of $^{14}C$ in modern carbon. Further, the inventors of the present invention have found that a biodegradation rate can be measured in an open field, which was hitherto impossible, by using as an internal standard a metal in a biodegradation medium, to thereby complete the present invention based on the findings.

That is, the gist of the present invention is described below.

(1) A method of measuring a biodegradation rate of a non-natural organic compound in the presence of a biodegradation medium, characterized by including: measuring a concentration of a radioactive carbon isotope $^{14}C$ in a biodegradation medium; and measuring a biodegradation rate of a non-natural organic compound from a difference between the concentration of $^{14}C$ in the biodegradation medium and a concentration of $^{14}C$ in modern carbon.

(2) A method of measuring a biodegradation rate of a non-natural organic compound according to the above item (1), characterized in that the biodegradation rate is measured by using an internal standard.

(3) A method of measuring a biodegradation rate of a non-natural organic compound according to the above item (2), characterized in that the internal standard is a metal selected from the group consisting of bioessential metals such as iron, copper, and manganese.

BEST MODE FOR CARRYING OUT THE INVENTION

Figure 1:
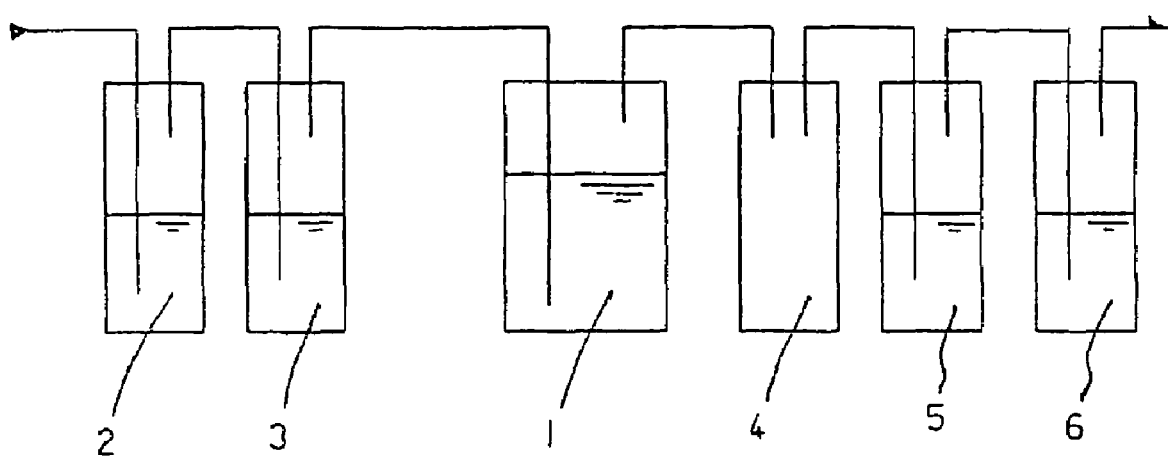
FIG. 1 shows an explanation drawing showing an example of a biodegradation reaction apparatus used in the present invention.

The method of measuring a biodegradation rate of a non-natural organic compound of the present invention includes: in the presence of a biodegradation medium, measuring a concentration of a radioactive carbon isotope $^{14}C$ in a biodegradation medium; and measuring a biodegradation rate of a non-natural organic compound from a difference between the concentration of $^{14}C$ in the biodegradation medium and a concentration of $^{14}C$ in modern carbon.

The non-natural organic compound used for measurement of a biodegradation rate in the present invention includes various organic compounds such petrochemicals and coal chemicals synthesized from raw materials of fossil fuels such as petroleum, coal, and natural gas. Of the non-natural organic compounds, substances likely providing adverse effects on natural environment such as a synthetic detergent, which flows out to natural world after use with waste water and contaminates water in rivers and lakes, must be investigated on progress of biodegradation by microorganisms in the natural world, in particular.

In a natural carbon-containing substance such as carbon dioxide in atmosphere or plants, 1 mole of carbon represents $6.0 \times 10^{23}$ carbon atoms. Since a concentration of $^{14}C$ in carbon is $1/10^{12}$ of that of $^{12}C$ in abundance ratio, 1 mole of carbon represents $6 \times 10^{11}$ radioactive carbon isotope $^{14}C$ atoms. A half-life of the radioactive carbon isotope $^{14}C$ is $5,730 \pm 40$ years, and a time period required for decay of all the $6 \times 10^{11}$ radioactive carbon isotope $^{14}C$ atoms is 226,000 years. Thus, in fossil fuels such as coal, natural gas, and petroleum obtained by incorporating and fixing carbon dioxide in atmosphere into living bodies such as plants and being stored underground for 226,000 years or more, all the radioactive carbon isotope $^{14}C$ atoms in carbon have already decayed.

The present invention allows measurement of a biodegradation rate by microorganisms or the like of various non-natural organic compounds such as petrochemicals and coal chemicals synthesized from raw materials of fossil fuels containing no radioactive carbon isotope $^{14}C$, which already decayed. The results of the measurement allow tracking of a biodegradation process of the substances in the natural world.

Here, a value so-called percent Modern Carbon (pMC) calculated based on a concentration of $^{14}C$ in circulating carbon as of 1950 as 100% has been used as a notation for the concentration of $^{14}C$ under an international agreement. A concentration of the radioactive carbon isotope $^{14}C$ in carbon dioxide in atmosphere has varied after 1950, and a concentration of $^{14}C$ at present (2002) falls within a range of 110 to 111%.

Next, the following operations are performed for the method of the present invention. For example, a sample for measuring a biodegradation rate of a non-natural organic compound such as a petrochemical product synthesized from a raw material of a fossil fuel and a substance which is a natural substance containing a radioactive carbon isotope $^{14}C$ and has a function of causing biodegradation of the non-natural organic compound such as compost, active sludge, or soil suspension are mixed and charged into a reaction tank 1 of a biodegradation reaction apparatus constituted as shown in FIG. 1. Then, a biodegradation reaction of the sample is carried out at a predetermined temperature while an air having carbon dioxide in atmosphere completely removed therefrom is introduced into a vicinity of a bottom of the reaction tank 1.

As shown in FIG. 1, the air is introduced in to the reaction tank 1 through a carbon dioxide absorption tank 2 containing an aqueous solution of sodium hydroxide or the like and a water washing tank 3, to thereby inhibit carbon dioxide in atmosphere to enter a reaction system. The air introduced into the reaction tank 1 except air partly consumed in the biodegradation reaction is introduced into a reservoir tank 4, a first-stage trap 5, and a second-stage trap 6 from a vicinity of a top of the reaction tank 1 with carbon dioxide generated in the biodegradation reaction.

In this way, the biodegradation reaction is carried out for a predetermined period of time such as for 10 days. Then a medium containing non-natural organic compound of the biodegraded sample is burned in air having carbon dioxide similarly removed therefrom or in pure oxygen, to thereby convert the medium into carbon dioxide. Carbon dioxide is passed through an aqueous solution of sodium hydroxide or the like in the same manner as described above, and absorbed and trapped therein. Then, a content (pMC) of a radioactive carbon isotope $^{14}C$ in carbon dioxide can be measured by using a scintillation counter or an accelerator-mass spectrometer.

A biodegradation rate of a measurement sample can be obtained by: determining pMC of a medium containing a sample obtained as described above before and after biodegradation and a content (pMC of control medium) of a radioactive carbon isotope $^{14}C$ obtained in the same manner by using a medium formed of a natural substance alone such as a fertilizer without addition of the non-natural organic compound in the sample; and using the values for the following calculation formulae.

$$B = \frac{\left(\begin{array}{c}pMC \text{ of control medium}\\ \text{before biodegradation}\end{array}\right) - \left(\begin{array}{c}pMC \text{ of sample medium}\\ \text{before biodegradation}\end{array}\right)}{\left(\begin{array}{c}pMC \text{ of control medium}\\ \text{before biodegradation}\end{array}\right)} \quad (1)$$

$$C = \frac{\left(\begin{array}{c}pMC \text{ of control medium}\\ \text{after biodegradation}\end{array}\right) - \left(\begin{array}{c}pMC \text{ of sample medium}\\ \text{after biodegradation}\end{array}\right)}{\left(\begin{array}{c}pMC \text{ of control medium}\\ \text{after biodegradation}\end{array}\right)} \quad (2)$$

Note that, pMC of the control medium does not change before and after biodegradation.

Carbon content in sample medium before biodegradation (D)

$$D = \frac{\text{Carbon content derived from sample (g)}}{B} \quad (3)$$

Carbon content in sample medium after biodegradation (E)

$$E = D - \text{Amount of carbon dioxide discharged from sample medium(g)} \times \frac{12}{44} \quad (4)$$

$$\text{Biodegradation rate}(\%) = \left[1 - \frac{E \times C}{D \times B}\right] \times 100 \quad (5)$$

$$= \left[1 - \frac{E \times C}{\text{Carbon content derived from sample (g)}}\right] \times 100 \quad (6)$$

In the method of the present invention, the medium subjected to biodegradation contains a metal species such as iron, copper, or manganese. The metal species does not biodegrade even in a biodegradation operation, evaporate, or the like, and a total content of the metal species hardly changes before and after the biodegradation operation. Thus, by taking advantage of the property, the metal species in the biodegradation medium can be used as an internal standard, and a biodegradation rate can be determined by the following calculation formulae.

$$H = \frac{F}{G} \times D \quad (7)$$

$$E = \frac{J}{I} \times K = \frac{J}{I} \times \frac{F}{G} \times D \quad (8)$$

Symbols in the above calculation formulae are defined as described below.

F: Metal concentration of sample medium before biodegradation.

G: Carbon concentration of sample medium before biodegradation.

I: Metal concentration of sample medium after biodegradation.

J: Carbon concentration of sample medium after biodegradation.

D: Carbon content (g) of sample medium before biodegradation.

E: Carbon content (g) of sample medium after biodegradation.

H: Metal content (g) of sample medium before biodegradation.

K: Metal content (g) of sample medium after biodegradation. In addition, a metal is used as an internal standard, and K=H.

The method has advantages in that: carbon dioxide generated in biodegradation need not be trapped; biodegradation need not be carried out in a closed reaction tank; and a biodegradation rate can be measured with an apparatus in open atmosphere.

Next, the present invention will be described more specifically by way of examples.

EXAMPLE 1

A biodegradation test of polycaprolactone in compost was performed by using an apparatus schematically shown in FIG. 1 as a biodegradation reaction apparatus.

One hundred and seventy one point four g of compost (water content: 65 mass %) and 400.0 g of sea sand (25 to 35 mesh, water content: 20 mass %) washed with water as natural substances, and 5.0 g of polycaprolactone (hereinafter, referred to as "PCL") as a non-natural organic compound were sufficiently mixed, to thereby prepare a biodegradation medium. Four mass % of the biodegradation medium was sampled for analysis, and the remainder was filled into the reaction tank 1.

Next, the reaction tank 1 was placed into a thermostatic bath at 58° C. A low-pressure air was passed through the carbon dioxide absorption tank 2 and the water washing tank 3 to remove carbon dioxide in atmosphere, and was introduced into the reaction tank 1 from an air introduction tube inserted into the vicinity of the bottom of the reaction tank 1. The carbon dioxide absorption tank 2 included a 2 N aqueous solution of sodium hydroxide to absorb carbon dioxide in atmosphere. An air flow rate was 30 ml/minute. Excess air and carbon dioxide generated in a biodegradation reaction in the reaction tank 1 were introduced into the reservoir tank 4 from the vicinity of the top of the reaction tank 1 through an introduction tube. An introduction tube from an exit of the reservoir tank 4 was introduced into an aqueous solution of sodium hydroxide in the first-stage trap 5. The second-stage trap 6 was provided downstream of the first-stage trap 5, to thereby discharge excess air alone.

In this way, PCL was subjected to biodegradation in compost for 11 days. The medium after biodegradation was burned in a combustion furnace by using air passed through a carbon dioxide absorption tank similar to that in the above-described biodegradation reaction apparatus to remove carbon dioxide. A combustion gas was trapped in a trap containing an aqueous solution of sodium hydroxide, to thereby determine an amount of carbon dioxide in the aqueous solution and a pMC value thereof.

Similarly, a medium sampled before biodegradation was burned in a combustion furnace, to thereby determine a pMC value of carbon dioxide. Further, an iron (Fe) concentration and a total carbon concentration were measured for the medium sampled before biodegradation and the medium after biodegradation.

As a comparative example, a biodegradation reaction of compost alone was carried out for 11 days using a biodegradation reaction apparatus having the same constitution as that of the above-described biodegradation reaction apparatus under the same conditions as for the above-described biodegradation reaction except that PCL as a non-natural organic compound was not added to the reaction tank 1 of the apparatus. Also in this case, an amount of carbon dioxide and a pMC value for the medium sampled before biodegradation and the medium after biodegradation were determined in the same manner as in Example 1.

Table 1 shows the results.

TABLE 1

|  | Example | Comparative Example |
| --- | --- | --- |
| pMC in medium before biodegradation (%) | 105.19 | 115.82 |
| pMC in medium after biodegradation (%) | 113.01 | * |
| Fe concentration in medium before biodegradation (ppm) | 50 | — |
| Fe concentration in medium after biodegradation (ppm) | 66 | — |
| Carbon concentration in medium before biodegradation (%) | 6.87 | — |
| Carbon concentration in medium after biodegradation (%) | 5.22 | — |

* No change from before biodegradation

A biodegradation rate based on an amount of carbon dioxide discharged from the medium was determined by using the above results and the calculation formulae (1) to (6), and a biodegradation rate based on an internal standard was determined by using the calculation formulae (7) and (8). Table 2 shows the results.

TABLE 2

| Calculation method | Biodegradation rate (%) |
| --- | --- |
| Based on discharged amount of $CO_2$ | 77 |
| Based on internal standard | 80 |

INDUSTRIAL APPLICABILITY

The present invention allows safe, simple, rapid, and accurate measurement of a biodegradation rate of a non-natural organic compound. In addition, when an internal standard is used, the present invention can provide a method of measuring a biodegradation rate of a non-natural organic compound having an effect allowing measurement with an apparatus in open atmosphere.

The invention claimed is:

1. A method for measuring a biodegradation rate of a non-natural organic compound in the presence of biodegradation medium, comprising:

preparing a sample medium by adding the non-natural organic compound to the biodegradation medium and without enriching said sample medium with a radioactive carbon isotope $^{14}C$;

measuring a concentration of $^{14}C$(pMC) of a control medium before biodegradation which is the biodegradation medium without said non-natural compound;

measuring a concentration of $^{14}C$(pMC), carbon, and metal as an internal standard of the sample medium before and after biodegradation;

calculating the biodegradation rate by using the obtained pMC values for the following calculation formulae:

$$B = \frac{\left(\begin{array}{c}pMC \text{ of control medium}\\ \text{before biodegradation}\end{array}\right) - \left(\begin{array}{c}pMC \text{ of sample medium}\\ \text{before biodegradation}\end{array}\right)}{\left(\begin{array}{c}pMC \text{ of control medium}\\ \text{before biodegradation}\end{array}\right)} \quad (1)$$

-continued $$C = \frac{\left(\begin{array}{c}pMC \text{ of control medium} \\ \text{after biodegradation}\end{array}\right) - \left(\begin{array}{c}pMC \text{ of sample medium} \\ \text{after biodegradation}\end{array}\right)}{\left(\begin{array}{c}pMC \text{ of control medium} \\ \text{after biodegradation}\end{array}\right)} \quad (2)$$

wherein a carbon content in the sample medium before biodegradation (D) is $$D = \frac{\text{Carbon content derived from sample (g)}}{B} \quad (3)$$

wherein a carbon content in the sample medium after biodegradation (E) is $$E = D - \text{Amount of carbon dioxide discharged from sample medium}(g) \times \frac{12}{44} \quad (4)$$

and wherein a biodegradation rate is $$\text{Biodegration rate}(\%) = \left[1 - \frac{E \times C}{D \times B}\right] \times 100 \quad (5)$$

$$= \left[1 - \frac{E \times C}{\text{Carbon content derived from sample}(g)}\right] \times 100; \quad (6)$$

or
wherein said biodegradation rate is determined using the following calculation formulae $$H = \frac{F}{G} \times D \quad (7)$$

$$E = \frac{J}{I} \times K = \frac{J}{I} \times \frac{F}{G} \times D \quad (8)$$

wherein
- F: metal concentration of sample medium before biodegradation;
- G: carbon concentration of sample medium before biodegradation;
- I: metal concentration of sample medium after biodegradation;
- J: carbon concentration of sample medium after biodegradation;
- D: carbon content (g) of sample medium before biodegradation;
- E: carbon content (g) of sample medium after biodegradation;
- H: metal content (g) of sample medium before biodegradation;
- K: metal content (g) of sample medium after biodegradation; and K=H; and wherein said non-natural compound is a petrochemical and/or a coal chemical synthesized from a raw material of fossil fuel.

2. The method according to claim 1, wherein said metal is selected from the group consisting of iron, copper, manganese and mixtures thereof.

3. The method according to claim 1, wherein the fossil fuel is petroleum, coal or natural gas.

4. A method for measuring a biodegradation rate of a non-natural organic compound in the presence of a biodegradation medium, comprising:
preparing a sample medium by adding the non-natural organic compound to the biodegradation medium and without enriching said sample medium with a radioactive carbon isotope $^{14}C$;
measuring a concentration of $^{14}C(pMC)$ of a control medium before biodegradation which is the biodegradation medium without said non-natural compound;
measuring a concentration of $^{14}C(pMC)$, carbon, and metal as an internal standard of the sample medium before and after biodegradation:
calculating the biodegradation rate by using the obtained pMC values for the following calculation formulae:

$$B = \frac{\left(\begin{array}{c}pMC \text{ of control medium} \\ \text{before biodegradation}\end{array}\right) - \left(\begin{array}{c}pMC \text{ of sample medium} \\ \text{before biodegradation}\end{array}\right)}{\left(\begin{array}{c}pMC \text{ of control medium} \\ \text{before biodegradation}\end{array}\right)} \quad (1)$$

$$C = \frac{\left(\begin{array}{c}pMC \text{ of control medium} \\ \text{after biodegradation}\end{array}\right) - \left(\begin{array}{c}pMC \text{ of sample medium} \\ \text{after biodegradation}\end{array}\right)}{\left(\begin{array}{c}pMC \text{ of control medium} \\ \text{after biodegradation}\end{array}\right)} \quad (2)$$

wherein a carbon content in the sample medium before biodegradation (D) is $$D = \frac{\text{Carbon content derived from sample (g)}}{B} \quad (3)$$

wherein a carbon content in sample medium after biodegradation (E) is $$E = D - \text{Amount of carbon dioxide discharged from sample medium}(g) \times \frac{12}{44} \quad (4)$$

and wherein a biodegradation rate is $$\text{Biodegration rate}(\%) = \left[1 - \frac{E \times C}{D \times B}\right] \times 100 \quad (5)$$

$$= \left[1 - \frac{E \times C}{\text{Carbon content derived from sample}(g)}\right] \times 100; \quad (6)$$

or
wherein said biodegradation rate is determined using the following calculation formulae $$H = \frac{F}{G} \times D \quad (7)$$

-continued $$E = \frac{J}{I} \times K = \frac{J}{I} \times \frac{F}{G} \times D \quad (8)$$

wherein
- F: metal concentration of sample medium before biodegradation;
- G: carbon concentration of sample medium before biodegradation;
- I: metal concentration of sample medium after biodegradation;
- J: carbon concentration of sample medium after biodegradation;
- D: carbon content (g) of sample medium before biodegradation;
- E: carbon content (g) of sample medium after biodegradation;
- H: metal content (g) of sample medium before biodegradation;
- K: metal content (g) of sample medium after biodegradation; and K=H;

wherein the non-natural organic compound is synthetic detergent.

5. A method for measuring a biodegradation rate of a non-natural organic compound in the presence of a biodegradation medium, comprising:

preparing a sample medium by adding the non-natural organic compound to the biodegradation medium and without enriching said sample medium with a radioactive carbon isotope $^{14}C$;

measuring a concentration of $^{14}C$(pMC) of a control medium before biodegradation which is the biodegradation medium without said non-natural compound;

measuring a concentration of $^{14}C$(pMC), carbon, and metal as an internal standard of the sample medium before and after biodegradation;

calculating the biodegradation rate by using the obtained pMC values for the following calculation formulae:

$$B = \frac{\begin{pmatrix} pMC \text{ of control medium} \\ \text{before biodegradation} \end{pmatrix} - \begin{pmatrix} pMC \text{ of sample medium} \\ \text{before biodegradation} \end{pmatrix}}{\begin{pmatrix} pMC \text{ of control medium} \\ \text{before biodegradation} \end{pmatrix}} \quad (1)$$

$$C = \frac{\begin{pmatrix} pMC \text{ of control medium} \\ \text{after biodegradation} \end{pmatrix} - \begin{pmatrix} pMC \text{ of sample medium} \\ \text{after biodegradation} \end{pmatrix}}{\begin{pmatrix} pMC \text{ of control medium} \\ \text{after biodegradation} \end{pmatrix}} \quad (2)$$

wherein a carbon content in the sample medium before biodegradation (D) is $$D = \frac{\text{Carbon content derived from sample (g)}}{B} \quad (3)$$

wherein a carbon content in the sample medium after biodegradation (E) is $$E = D - \text{Amount of carbon dioxide} \quad (4)$$
$$\text{discharged from sample medium}(g) \times \frac{12}{44}$$

and wherein a biodegradation rate is $$\text{Biodegration rate}(\%) = \left[1 - \frac{E \times C}{D \times B}\right] \times 100 \quad (5)$$

$$= \left[1 - \frac{E \times C}{\text{Carbon content derived from sample}(g)}\right] \times 100; \quad (6)$$

or wherein said biodegradation rate is determined using the following calculation formulae $$H = \frac{F}{G} \times D \quad (7)$$

$$E = \frac{J}{I} \times K = \frac{J}{I} \times \frac{F}{G} \times D \quad (8)$$

wherein
- F: metal concentration of sample medium before biodegradation;
- G: carbon concentration of sample medium before biodegradation;
- I: metal concentration of sample medium after biodegradation;
- J: carbon concentration of sample medium after biodegradation;
- D: carbon content (g) of sample medium before biodegradation;
- E: carbon content (g) of sample medium after biodegradation;
- H: metal content (g) of sample medium before biodegradation;
- K: metal content (g) of sample medium after biodegradation; and K=H;

wherein the non-natural organic compound comprises no radioactive carbon isotope $^{14}C$ which already decayed.

6. The method according to claim 1, wherein the content of a radioactive carbon isotope $^{14}C$ is measured using a scintillation counter or an accelerator-mass spectrometer.

7. The method according to claim 1, wherein a total content of the metal does not change before and after biodegradation.

8. The method according to claim 1, wherein carbon dioxide generated in biodegradation is not trapped.

9. The method according to claim 1, wherein the biodegradation is not carried out in a closed reaction tank.

10. The method according to claim 1, wherein the biodegradation rate is measured with an apparatus in open atmosphere.

11. The method according to claim 1, wherein the biodegradation rate is measured without providing measures against radiation.

12. The method according to claim 1, wherein the non-natural compound is a petrochemical.

13. The method according to claim 1, wherein the non-natural compound is a coal chemical.

14. The method according to claim 1, wherein the non-natural compound is a mixture of the petrochemical and the coal chemical.

* * * * *